United States Patent [19]
Blaisdell

[11] Patent Number: 6,080,129
[45] Date of Patent: Jun. 27, 2000

[54] METHOD AND APPARATUS FOR PERFORMING HYSTEROSALPINGOGRAPHY

[75] Inventor: Michael W. Blaisdell, Sylvania, Ohio

[73] Assignee: Conceptus, Inc., San Carlos, Calif.

[21] Appl. No.: 08/772,395

[22] Filed: Dec. 23, 1996

[51] Int. Cl.[7] ................................ A61M 31/00
[52] U.S. Cl. .......................... 604/55; 128/898
[58] Field of Search ............... 604/55, 54, 176, 604/178, 96; 606/192, 193; 128/898

[56] References Cited

U.S. PATENT DOCUMENTS

| | | | |
|---|---|---|---|
| 3,721,229 | 3/1973 | Panzer | 606/198 |
| 4,430,076 | 2/1984 | Harris | 604/96 |
| 4,496,345 | 1/1985 | Hasson | 604/103 |
| 4,586,491 | 5/1986 | Carpenter | 128/6 |
| 4,651,201 | 3/1987 | Schoolman | 600/109 |
| 4,779,612 | 10/1988 | Kishi | 128/6 |
| 4,836,189 | 6/1989 | Allred, III et al. | 128/6 |
| 4,867,404 | 9/1989 | Harrington et al. | 600/102 |
| 4,911,148 | 3/1990 | Sosnowski et al. | 128/6 |
| 5,002,557 | 3/1991 | Hasson | 606/191 |
| 5,083,549 | 1/1992 | Cho et al. | 128/7 |
| 5,104,377 | 4/1992 | Levine | 604/101 |
| 5,146,925 | 9/1992 | Snow | 128/658 |
| 5,147,315 | 9/1992 | Weber | 604/164 |
| 5,152,277 | 10/1992 | Honda et al. | 128/4 |
| 5,156,590 | 10/1992 | Vilmar | 604/4 |
| 5,176,697 | 1/1993 | Hasson et al. | 606/191 |
| 5,184,601 | 2/1993 | Putman | 128/4 |
| 5,209,754 | 5/1993 | Ahluwalia | 606/119 |
| 5,211,627 | 5/1993 | William | 604/82 |
| 5,259,836 | 11/1993 | Thurmond et al. | 604/55 |
| 5,273,526 | 12/1993 | Dance et al. | 604/35 |
| 5,300,023 | 4/1994 | Lowery et al. | 604/51 |
| 5,372,584 | 12/1994 | Zink et al. | 604/55 |
| 5,374,247 | 12/1994 | Lowery et al. | 604/55 |
| 5,389,089 | 2/1995 | Bauer et al. | 604/271 |

FOREIGN PATENT DOCUMENTS

| | | |
|---|---|---|
| 730355 | 4/1978 | U.S.S.R. . |
| WO 96/22122 | 7/1996 | WIPO . |

OTHER PUBLICATIONS

Kerin et al. (1990) Fertil. Steril. 54:390–400.
J. Laparoendoscopic Surg. 1:47–56.
Kerin et al. (1992) Fertil. Steril. 57:731–741.
Kerin and Surrey (1992) Clin. Obstet. Gynacol. 35:299–312.
Product Brochure ZUMI–4.5, BEI Medical Systems, Inc.

Primary Examiner—David J. Isabella
Attorney, Agent, or Firm—Townsend and Townsend and Crew LLP

[57] ABSTRACT

A uterine access catheter system comprises an inner catheter and a catheter sleeve slidably disposed over the inner catheter. Initial access to the uterus is accomplished by positioning the inner catheter through the cervix with the sleeve remaining outside of the cervix. After inflating a balloon near the distal end of the inner catheter, contrast media can be injected and hysterosalpingography performed. Should the initial hysterosalpingography be unsuccessful, direct access to the fallopian tubes can be achieved by further inserting the sleeve catheter through the cervix, removing the inner catheter, and utilizing a uterine catheter and fallopian catheter for accessing the fallopian tubes.

29 Claims, 6 Drawing Sheets

METHOD AND APPARATUS FOR PERFORMING HYSTEROSALPINGOGRAPHY

The subject matter of the present application is related to application Ser. No. 08/772,707 now U.S. Pat. No. 5,935,098 (Attorney Docket No. 16355-003300), filed on the same day as the present application, the full disclosure of which is incorporated herein by reference.

BACKGROUND OF THE INVENTION

1. Field of the Invention

The present invention relates generally to methods and apparatus for sequentially accessing the uterus and fallopian tubes of a patient. More particularly, the present invention relates to a method and catheter system for performing hysterosalpingography followed by optionally accessing the fallopian tubes.

Diseases of the fallopian tubes are a major cause of infertility and tubal pregnancy. Until recently, diagnosis and treatment of tubal disease has been hampered by the difficulty in accessing and imaging the interior of the fallopian tubes in a least invasive manner. Such difficulties, however, have been largely overcome by the present availability of very small guidewires, catheters and fiberoptic viewing scopes, usually referred to as falloposcopes. Particular systems and methods employing a hysteroscope in combination with the guidewire and small diameter fallopian access catheter for accessing and viewing the interior of the fallopian tubes are described in Kerin et al. (1990) *Fertil. Steril.* 54:390–400 and *J. Laparo. Endoscopic Surg.* 1:47–56, and copending patent application Ser. No. 08/207,475, assigned to the assignee of the present application.

A common medical procedure for imaging the uterus and fallopian tubes is referred to as hysterosalpingography. Such procedures rely on injecting contrast media into the uterus and fallopian tubes using a uterine access catheter having an elastomeric balloon near its distal end for sealing against the cervix. The anatomical structures of the uterus and fallopian tubes are then fluoroscopically imaged in a conventional manner. In some cases, however, contrast media injected into the uterus does not fully pass into the fallopian tubes. If the fallopian tubes are not filled with the contrast media, subsequent imaging may be inadequate.

In such circumstances, it has been proposed to pass a pair of coaxial catheters through the uterine access catheter in order to access the fallopian tubes. In particular, an outer catheter is used to engage the fallopian os and a smaller tubular catheter is passed through the outer catheter and into the fallopian tube. Contrast media can then be injected directly into the fallopian tube for improved imaging. Such systems are described in U.S. Pat. No. 5,372,584.

While such coaxial catheter systems for selectively accessing the uterus and fallopian tubes are generally successful, they rely on using a relatively large diameter uterine access catheter. In particular, the uterine access catheter must be sufficiently large to pass the coaxial catheter system which is used to enter the fallopian tubes. The need to pass a larger catheter through the cervix significantly increases patient discomfort and can be more difficult for the physician to insert. While it would be possible to initially employ a small catheter for contrast media introduction, subsequent fallopian tube access would then require use of a second, larger uterine access catheter, thus increasing the cost and complexity of the procedure.

For these reasons, it would be desirable to provide improved methods and apparatus for performing hysterosalpingography. Such methods and apparatus will preferably provide for initial introduction of contrast media using a small diameter uterine access catheter followed by optionally accessing the fallopian tubes using a separate catheter system without the need to introduce a separate uterine access catheter. Such methods and apparatus should reduce the complexity and cost of performing hysterosalpingography and related fallopian tube access procedures. It would be further desirable if such apparatus were useful for other gynecological procedures, such as treatment of proximal tubal occlusion, endoscopic tubal examination, transcervical gamete intrafallopian transfer (GIFT), therapeutic drug delivery for treatment of ectopic pregnancies, endometrial biopsy, intrauterine ultrasound, removal of myomas, polyps, and/or septums, and the like.

2. Description of the Background Art

U.S. Pat. No. 5,372,584, describes a catheter system for performing hysterosalpingography and selective salpingography. Catheter systems and methods for accessing the fallopian tubes are described in U.S. Pat. Nos. 5,389,089; 5,379,247; 5,300,023; and 5,147,315. Catheters intended for uterine access and/or manipulation are described in U.S. Pat. Nos. 5,259,836; 5,104,377, 4,496,345; 4,430,076; and WO 96/22122. Other catheter systems are described in U.S. Pat. Nos. 5,273,526 and 5,211,627. A cervical cannula is described in SU 730355. Laparoscopic cannulas comprising coaxial tubular members are described in U.S. Pat. Nos. 5,002,557 or 5,176,697. A cervical manipulator comprising an inner balloon member and outer cervical cap is described in U.S. Pat. No. 5,209,754. Devices manufactured under U.S. Pat. No. 4,430,076, are sold by BEI Medical Systems under the trade names ZUMI and AUI, as described in a catalogue of BEI.

A coaxial catheter system for accessing and imaging a fallopian tube is described in copending application Ser. No. 08/207,475, filed on Mar. 7, 1994, assigned to the assignee of the present application, the full disclosure of which is incorporated herein by reference.

SUMMARY OF THE INVENTION

According to the present invention, methods and systems are provided for accessing and imaging a patient's uterus and fallopian tubes. The methods and systems are particularly suitable for performing hysterosalpingography and providing fallopian tube access following hysterosalpingography, but will also find use in a variety of other procedures requiring sequential access to the uterus and fallopian tubes. The methods and systems are particularly beneficial in that initial access to the uterus is provided with a small diameter, preferably soft, catheter which is passed into the uterus. Should a relatively large diameter access lumen into the uterus be subsequently required, the present invention provides for passage of a sleeve over the initial access catheter through the cervix and into the uterus. Thus, initial access and hysterosalpingography can be achieved using a catheter which is both easier to introduce and less traumatic to the patient, while a larger-diameter access catheter and lumen can be provided with a minimum increase in complexity and cost.

In a first aspect, the present invention provides a method for performing hysterosalpingography utilizing a catheter system which includes (1) an inner catheter having a balloon near its distal end and (2) a sleeve catheter disposed coaxially over the inner catheter. The catheter system is initially introduced through the patient's vagina so that the balloon on the inner catheter is positioned past the cervix while the larger-diameter sleeve remains outside the cervix over a proximal portion of the inner catheter shaft. The balloon on the inner catheter is then inflated and sealed against the cervix, and contrast media introduced through a lumen in the inner catheter into the uterus. Fluoroscopic imaging is performed, and if sufficient information is obtained from this initial imaging, the catheter system can be removed without ever having to introduce the larger-diameter sleeve through the cervix.

In the event that further imaging or other access to the uterus and/or fallopian tubes is required, the sleeve is advanced over the inner catheter through the cervix. The inner catheter is then withdrawn from the sleeve, leaving a relatively large diameter access lumen through the cervix. While passage of the sleeve through the cervix will necessarily be more traumatic than initial introduction of the inner catheter, such introduction will not be necessary at all on those patients who require no further procedures after the initial imaging. In contrast, the prior art systems have usually employed larger diameter, relatively rigid uterine access catheters for the initial introduction of contrast media into the uterus. Thus, patients who do not require subsequent fallopian tube access are unnecessarily subjected to the discomfort associated with introduction of such larger, rigid catheters.

In further aspects of the method of the present invention, after the sleeve is positioned through the cervix, a variety of other imaging and/or therapeutic procedures can be performed. Most commonly, a uterine catheter will be introduced through the sleeve and guided to the fallopian tube os. A small diameter fallopian catheter can then be introduced through the uterine catheter through the fallopian tube os and into the lumen of the fallopian tube, optionally over a guidewire. The fallopian catheter can then be used for injecting contrast media prior to further fluoroscopic imaging. Alternatively, a falloposcope can be introduced through the fallopian catheter to provide for direct imaging of the fallopian tube lumen. Additionally, therapeutic procedures, such as use of a guidewire to remove obstructions in the fallopian tubes may also be performed.

Systems according to the present invention will comprise an inner catheter and a sleeve slidably received over the inner catheter. The inner catheter has a proximal end, a distal end, and an lumen therethrough. An inflatable balloon is disposed near the distal end of the inner catheter, and the inner catheter has an outside diameter in the range from 1 mm to 2.5 mm, usually from 1.5 mm to 2 mm, and a length generally in the range from 25 cm to 40 cm, usually being about 30 cm. The access lumen will typically have a diameter from 1.5 mm to 2 mm. Preferably, the inner catheter further includes a hub at its proximal end, and the sleeve catheter will be introduced and removed over the distal end of the inner catheter.

The sleeve catheter 30 also has a proximal end, a distal end, and a lumen therebetween. The sleeve catheter lumen will be sized so that it may be slidably positioned over the inner catheter 12. The length of the sleeve catheter 30 will be less than that of the inner catheter 12 by a distance of at least 5 cm. In this way, the distal end of the inner catheter 12 can be introduced through a patient's cervix while the distal end of the sleeve catheter 30 remains over a proximal portion of the inner catheter and outside of the cervix. As described above in connection with the method, such positioning allows initial introduction of the relatively small diameter inner catheter while maintaining the larger-diameter sleeve catheter 30 available for immediate introduction through the cervix if it is necessary.

The sleeve catheter 30 will have a lumen diameter sufficient to accommodate the outer diameter of the inner catheter 12, usually being from 2 mm to 4 mm, more usually being about 2.5 mm to 3 mm. The outer diameter of the sleeve catheter 30 will generally be in the range from 3 mm to 4.5 mm, and the sleeve catheter will have a length in the range from 15 cm to 25 cm, usually from 15 cm to 20 cm.

The balloon 18 on the inner catheter 12 will usually be elastomeric and inflatable to a width in the range from 10 mm to 15 mm. The inner catheter 12 will preferably be composed of a soft material, such as a thermoplastic polymer or an elastomer, having a hardness in the range from 65D to 75D, more usually 68D to 74D. The sleeve catheter 30 will usually be formed from a similar material, but may be harder or more rigid in order to provide a stable platform for subsequent introduction of other catheters into the uterus and fallopian tubes, typically having a hardness from 65D to 100D, preferably from 70D to 80D. Optionally, a stiffening rod may be provided for removably inserting into the lumen of the inner catheter to enhance its stiffness and rigidity to facilitate initial introduction through the cervix. The stiffening rod may be malleable or resilient. Malleable stiffening rods are advantageous as they allow shaping of the rod to accommodate an individual patient's anatomy. The rod may be shaped and will cause at least a distal portion of the balloon catheter to assume the same shape. Malleable rods are also less traumatic. Resilient (non-malleable) stiffening rods provide a greater column strength and may sometimes be preferred for that reason. Systems according to the present invention could include both resilient and malleable stiffening rods, allowing the physician to choose a preferred rod for each procedure.

DESCRIPTION OF THE SPECIFIC EMBODIMENTS

Figure 1:
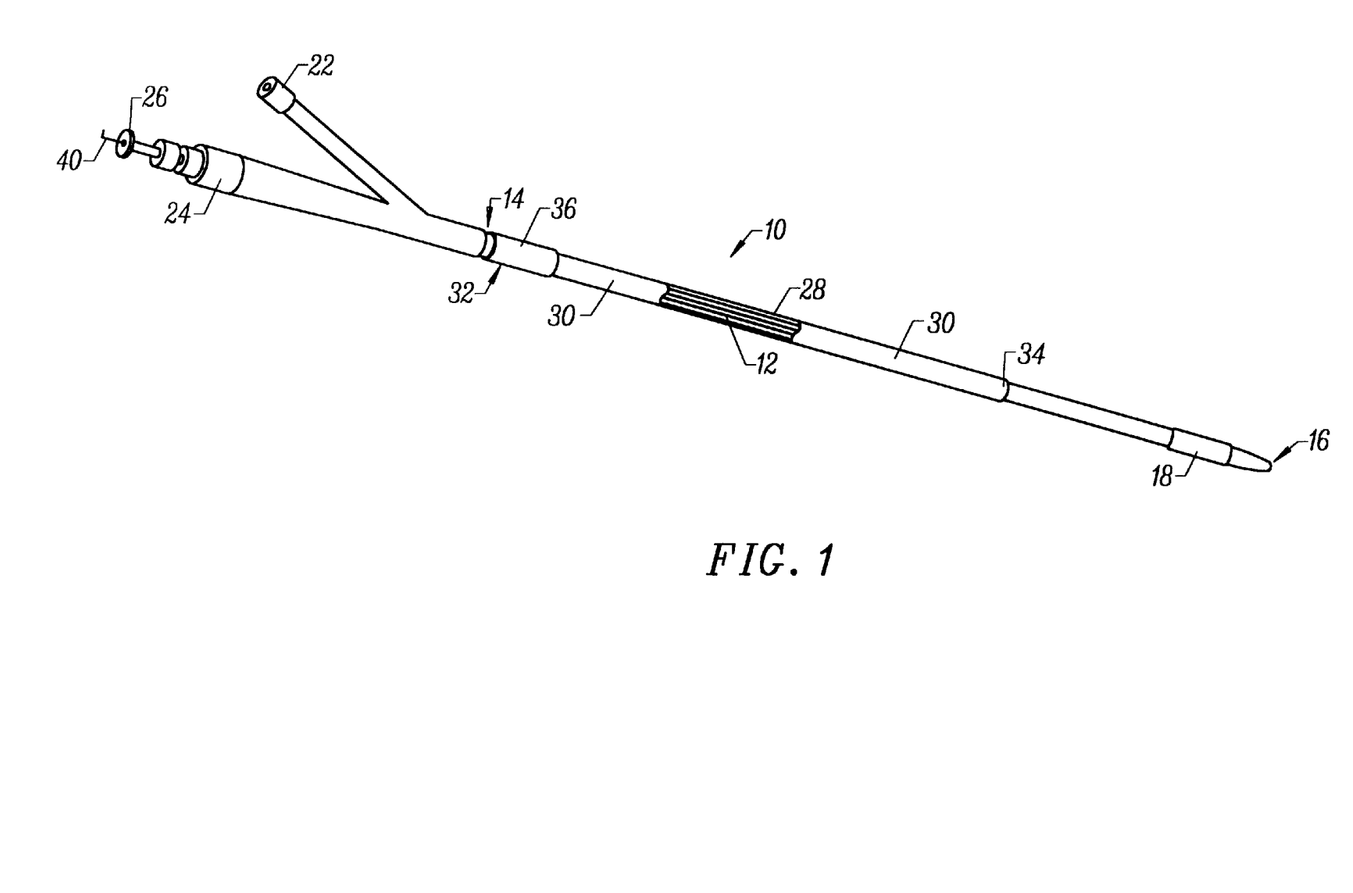
FIG. 1 is a perspective view of a uterine access catheter system constructed in accordance with the principles of the present invention.
Figure 2:
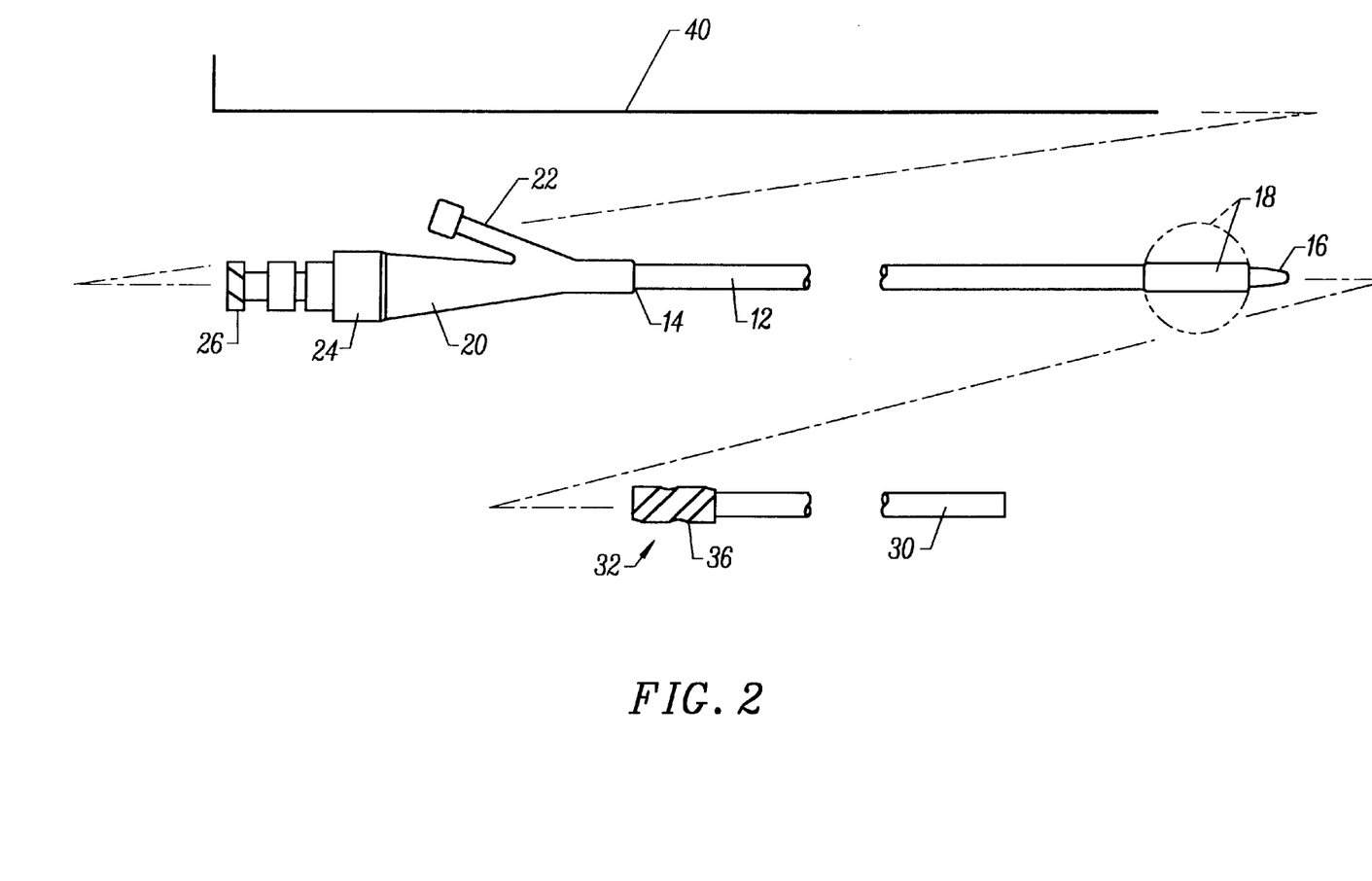
FIG. 2 is an exploded view of the catheter system of FIG. 1.

A uterine access catheter system 10 useful in performing the methods of the present invention is illustrated in FIGS. 1 and 2. The catheter system 10 comprises an inner catheter 12 having a proximal end 14, a distal end 16, and an inflatable balloon 18 near the distal end. A proximal hub 20 is secured to the proximal end 14 of the inner catheter 12 and includes an inflation port 22 and axial lumen access port 24. Typically, a luer fitting 26 will be located at the proximal end of the hub 20. A second embodiment comprising three separate components is described below.

The inner catheter 12 preferably comprises a flexible body formed from a soft material, usually a soft thermoplastic polymer or elastomer, such as pebax (polyether block amide) usually having a hardness in the range from 65D TO 75D, more usually 68D to 74D. The inner catheter 12 will include an axial access lumen 28 and usually a separate inflation lumen (not shown). The access lumen 28 will permit introduction of contrast media to the uterus, as will be described hereinafter. The inflation lumen will permit inflation of balloon 18 through port 22. Additional lumens may also be provided, although there will usually be no additional lumens since it is desired to maintain a low profile on the catheter to facilitate entry through the cervix. Typically, the inner catheter 12 will have an outside diameter in the range from 1.0 mm to 2.5 mm, preferably from 1.5 mm to 2 mm, typically being 1.6 mm to 1.8 mm. The access lumen will typically have a diameter in the range from 0.5 mm to 1.5 mm, usually from 0.5 mm to 0.8 mm, typically being from 0.6 mm to 0.7 mm. The length of the catheter 12 will usually be in the range from 25 cm to 40 cm, more usually being about 30 cm.

The balloon 18 will usually be distensible, more usually being formed from an elastomeric material, often the same material as that used for forming the catheter 12 itself. The balloon will usually be inflatable to a width in the range from 10 mm to 15 mm, in order to permit the balloon to occlude the cervix during hysterosalpingography procedures, as described in more detail below. The balloon may be fixedly mounted on the catheter body, e.g. formed as a single extrusion and expanded to the appropriate size, or may be formed separately and attached by gluing, welding, or other conventional attachment procedures.

The uterine access catheter system further comprises a sleeve catheter 30 having a proximal end 32 and a distal end 34. The sleeve catheter 30 will usually be a simple tube having only a single lumen therethrough. Optionally, a handle 36 may be formed or disposed at or near the proximal end 32 in order to facilitate gripping and manipulation of the sleeve 30. The handle 36 may be a simple tube formed or attached coaxially over the proximal end of the sleeve catheter 30. Alternatively, the handle 36 could comprise a standard luer or other connectable fitting allowing direct connection of the sleeve catheter 30 to external equipment for infusing and/or aspirating the uterus when the sleeve catheter has been extended past the cervical or into the uterus and the inner catheter 12 has been removed.

The sleeve may be formed from the same or a different material than that of the inner catheter. The sleeve material will be more rigid than that used to form the inner catheter, typically having a hardness in the range from 65D to 100D, preferably in the range from 70D to 80D, and being composed of the same or a similar material as the inner catheter. The sleeve catheter 32 will have a smooth, atraumatic tip, and will be slidably disposed over the outside of the inner catheter 12. The length of the sleeve catheter 30 will be less than that of the inner catheter 12, typically by at least 5 cm so that the inner catheter can be introduced through the cervix while the distal tip of the sleeve catheter remains over a proximal region of the inner catheter outside of the cervix. The length of the sleeve catheter will typically be in the range from 15 cm to 25 cm, more typically from 15 cm to 20 cm, preferably from 16 cm to 18 cm. The inner diameter of the sleeve catheter 30 lumen will typically be in the range from 2 mm to 4 mm, preferably from 2.5 mm to 3 mm. The outside diameter of the sleeve catheter 30 will be the minimum necessary for providing the desired lumen diameter, typically being from 3 mm to 4 mm, usually from 3.3 mm to 4 mm. The wall thickness of the sleeve 30 will thus usually being in the range from 0.8 mm to 1 mm.

A stiffening rod or mandrel 40 is optionally provided for inserting through the lumen 28 of the inner catheter 12. The stiffening rod improves the column strength of the inner catheter 12 to facilitate initial introduction through the cervix. After introduction, the stiffening rod 40 can be removed to clear the lumen for introduction of contrast media to perform the hysterosalpingography procedure. The stiffening rod 40 may be composed of a malleable material and/or a resilient material, such as stainless steel. The advantages of each are set forth above. In either case, the rod 40 will have a length sufficient to extend at least most of the length through the axial access lumen 28 of the inner catheter 12. Usually, when fully inserted in the inner catheter 12, the distal end of the rod 40 will be disposed immediately proximal to the distal end 16 of the inner catheter 12. Such positioning reduces the risk of injury from the distal tip of the rod 40 protruding from the distal end 16 of the inner catheter 12 as the inner catheter is being introduced through the vagina and the cervical OS. Of course, it would be possible to provide a separate protective element over the distal tip of the rod 40, but this usually is not necessary.

The components of the uterine access catheter system 10 will preferably be packaged together in a sterile package, such as a pouch. The uterine access catheter system may be used with other conventional and commercially available catheters for performing fallopian tube access, as described herein below.

Use of the uterine access catheter 10 of the present invention for performing hysterosalpingography will now be described in connection with FIGS. 3A–3D. Initially, the access catheter system 10 is introduced through the vaginal opening V so that balloon 18 is disposed past cervix C. The balloon 18 is then inflated within the uterus U in order to block outflow from the uterus through the cervix C. Contrast media can then be introduced through port 24 (the stiffening rod 40 will have been removed after the balloon 18 has passed through the cervix C) and fluoroscopic imaging performed in the conventional manner. Up to this point, the sleeve catheter 30 remains retracted on the proximal portion of the inner catheter 12 so that distal end 34 of the sleeve remains outside of the cervix C. If the initial hysterosalpingography procedure is successful, the catheter system 10 may be withdrawn, and the system not used for further access to the fallopian tubes. If, however, the initial hysterosalpingography is not successful, it may be desired to introduce a small diameter access catheter (referred to as a fallopian catheter) into the fallopian tubes for direct injection of contrast media or other imaging procedures.

Figure 3A:
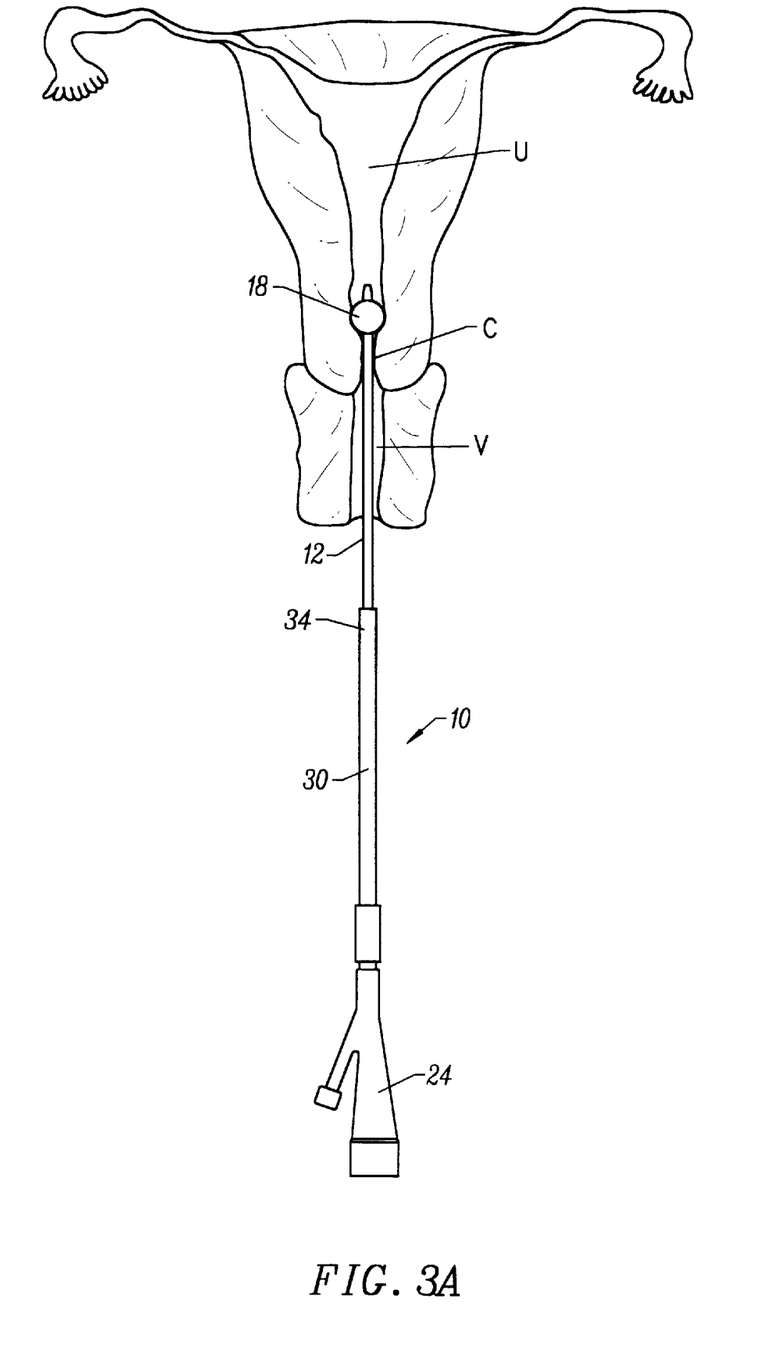
FIGS. 3A–3D illustrate use of the catheter system of FIG. 1 for performing a hysterosalpingography procedure followed by accessing the fallopian tube with a fallopian catheter.
Figure 3B:
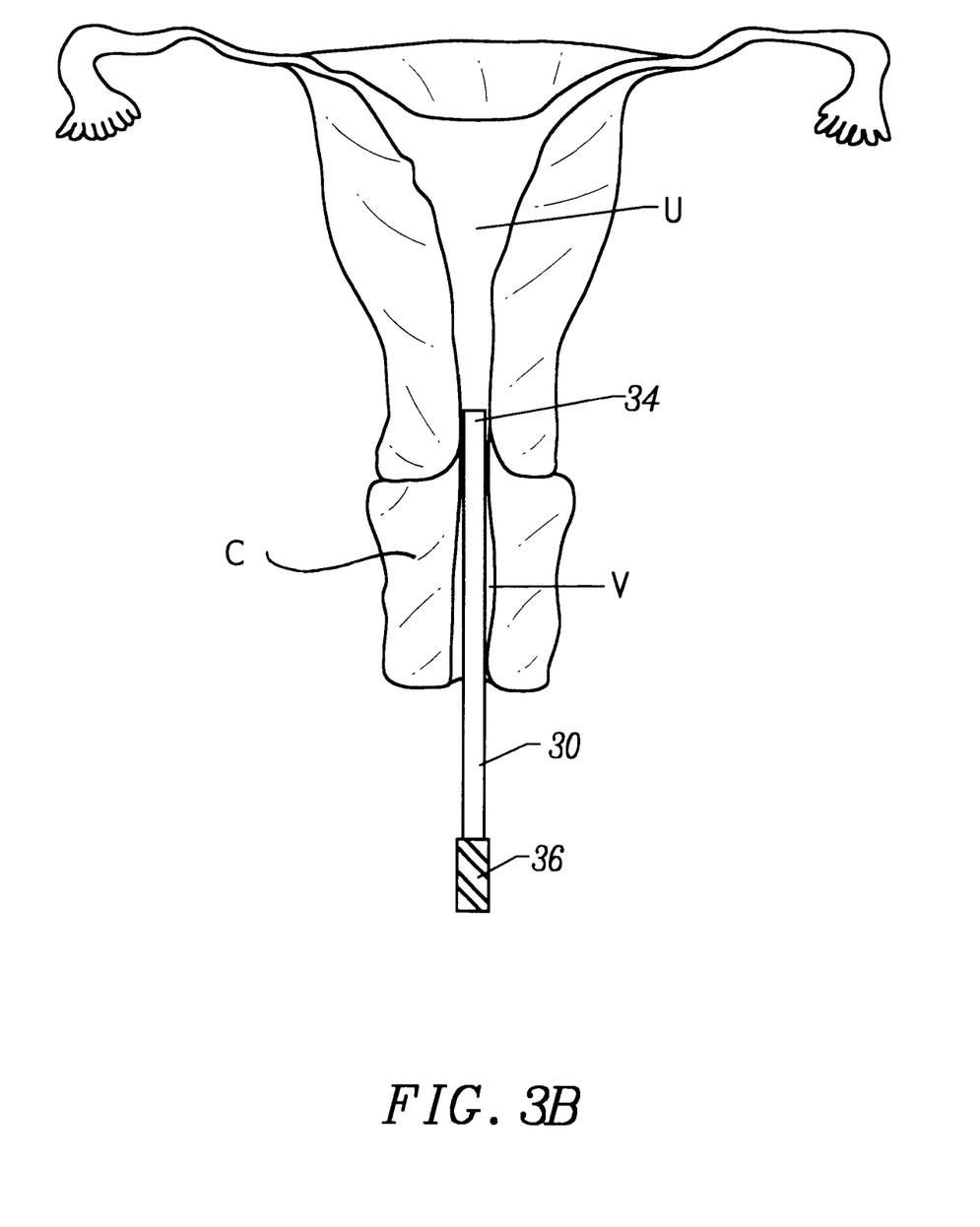

Referring now to FIGS. 3A–3D, in order to introduce further catheter or other components, the sleeve catheter 30 is advanced over the inner catheter 12 so that the distal end 34 passes beyond the cervix C. The inner catheter 12 is then withdrawn, and the sleeve catheter 30 provides a relatively large access lumen into the uterus U, as illustrated in FIG. 3B. Optionally, a fluid or other material could be infused into or aspirated from the uterus by connecting an appropriate external system to fitting 36.

Figure 3C:
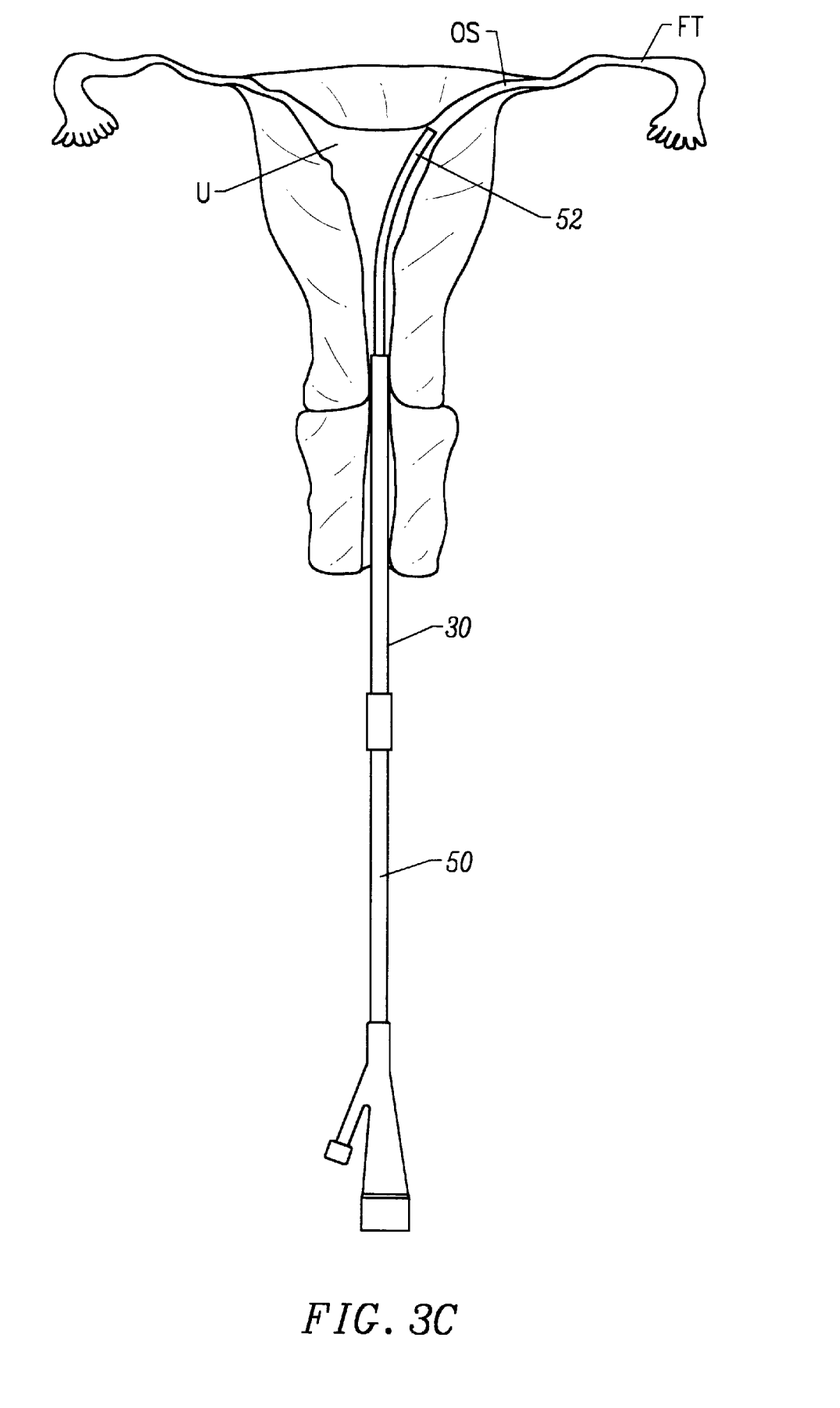

After the sleeve catheter 30 is in place, a uterine catheter 50 may be introduced through the sleeve into the uterus U. Suitable uterine access catheters are available from commercial suppliers, such as Conceptus, Inc., San Carlos, Calif., under the trade name SOFT TORQUE™ catheter. The uterine catheter 50 is positioned so that a deflected end 52 lies adjacent the os of the fallopian tube FT. The uterine catheter 50 thus provides a secondary access lumen directly to the os.

Figure 3D:
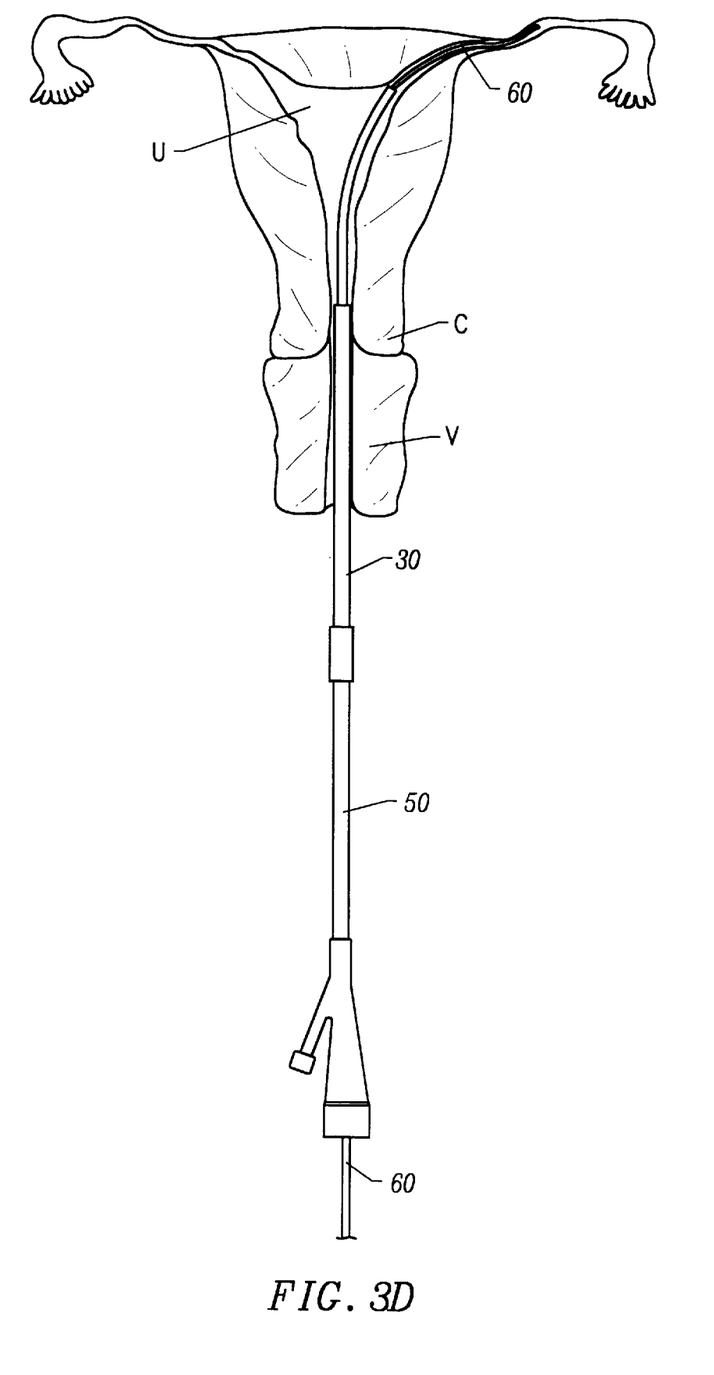

After the uterine catheter 50 has been positioned, a fallopian catheter 60 is passed through the uterine catheter 50, as illustrated in FIG. 3D. Optionally, a guidewire (not illustrated) may be used to position the fallopian catheter 60 within the fallopian tube FT. The fallopian catheter 60 may then be used for improved imaging of the fallopian tube. For example, contrast media may be directly injected through the fallopian catheter 60 into the fallopian tube FT. Fluoroscopic imaging of the tube may then be performed in a conventional manner. Alternatively, a falloposcope (not shown) may be introduced through the fallopian catheter 60 and used to image the fallopian tube. Such catheters are commercially available from Conceptus, Inc. Use of such falloposcopes for imaging a fallopian tube is described in copending application Ser. No. 08/207,475, the full disclosure of which has previously been incorporated herein by reference. The fallopian catheter 60 may also be used for other purposes such as treatment of tubal occlusions, endoscopic tubal examination, transcervical gamete intrafallopian transfer (GIFT), therapeutic drug delivery for treatment of ectopic pregnancies, endometrial biopsy, intrauterine ultrasound, removal of myomas, polyps, and/or septums, and the like.

Although the foregoing invention has been described in some detail by way of illustration and example, for purposes of clarity of understanding, it will be obvious that certain changes and modifications may be practiced within the scope of the appended claims.

What is claimed is:

1. A method for performing hysterosalpingography on a patient, said method comprising:

providing a catheter assembly including (1) an inner catheter having a balloon near its distal end and (2) a sleeve catheter disposed coaxially over the inner catheter;

introducing the catheter assembly through the patient's vagina so that the balloon is positioned past the cervix and in the uterus while a distal end of the sleeve catheter remains outside of and proximal to the cervix;

inflating the balloon to seal against the cervix;

introducing contrast media through the inner catheter into the uterus;

imaging the uterus;

advancing a distal end of the sleeve catheter over the inner catheter through the cervix and into the uterus; and withdrawing the inner catheter from the sleeve catheter to leave an access lumen in the sleeve catheter through the cervix into the uterus.

2. A method as in claim 1, further comprising:

introducing a uterine catheter through the lumen of the sleeve catheter and into the uterus after the sleeve catheter has been advanced into the uterus and the inner catheter removal from the sleeve catheter; and guiding a distal end of the uterine catheter to a fallopian os at the entrance to a fallopian tube.

3. A method as in claim 2, further comprising:

passing a fallopian catheter through a lumen of the uterine catheter and into the fallopian tube, wherein the uterine catheter remains within the sleeve catheter.

4. A method as in claim 3, further comprising:

passing a falloposcope through a lumen of the fallopian catheter; and imaging the fallopian tube using the falloposcope.

5. A method as in claim 3, further comprising introducing contrast media through the fallopian catheter into the fallopian tube; and imaging the fallopian tube.

6. A method as in claim 1, further comprising infusing or aspirating a fluid or material through a lumen of the sleeve catheter into the uterus after the sleeve catheter has been advanced into the uterus and the inner catheter removed from the lumen of the sleeve catheter.

7. A method as in claim 1, wherein the catheter system further comprises a stiffening rod that is removably received in a lumen of the inner catheter, wherein the stiffening rod is in place when the catheter system is introduced through the vagina and cervix and is removed prior to introducing contact media into the uterus.

8. A method as in claim 7, wherein the stiffening rod is malleable and further comprising shaping a portion of the stiffening rod so that the inner catheter assumes a shape selected to match the patient's anatomy.

9. A method for performing hysterosalpingography on a patient, said method comprising:

providing a catheter assembly including (1) an inner catheter having a balloon near its distal end and (2) a sleeve catheter disposed coaxially over the inner catheter;

introducing the catheter assembly through the patient's vagina so that the balloon is positioned past the cervix and in the uterus while a distal end of the sleeve catheter remains outside of and proximal to the cervix;

inflating the balloon to seal against the cervix;

introducing contrast media through the inner catheter into the uterus;

imaging the uterus;

optionally advancing a distal end of the sleeve catheter over the inner catheter through the cervix and optionally withdrawing the inner catheter from the sleeve catheter to leave an access lumen in the sleeve catheter through the cervix into the uterus;

introducing a uterine catheter through the lumen of the sleeve catheter and into the uterus after the sleeve catheter has been advanced into the uterus and the inner catheter removal from the sleeve catheter; and guiding a distal end of the uterine catheter to the os at the entrance to a fallopian tube.

10. A method as in claim 9, further comprising:

passing a fallopian catheter through a lumen of the uterine catheter and into the fallopian tube.

11. A method as in claim 10, further comprising:

passing a falloposcope through a lumen of the fallopian catheter; and imaging the fallopian tube using the falloposcope.

12. A method as in claim 10, further comprising introducing contrast media through the fallopian catheter into the fallopian tube; and imaging the fallopian tube.

13. A method as in claim 9, further comprising infusing of aspirating a fluid or material through the sleeve catheter into the uterus after the sleeve catheter has been advanced into the uterus and the inner catheter removed from the lumen of the sleeve catheter.

14. A method as in claim 9, wherein the catheter system further comprises a stiffening rod that is removably received in a lumen of the inner catheter, wherein the stiffening rod is in place when the catheter system is introduced through the vagina and cervix and is removed prior to introducing contact media into the uterus.

15. A method as in claim 14, wherein the stiffening rod is malleable and further comprising shaping a portion of the stiffening rod so that the inner catheter assumes a shape selected to match the patient's anatomy.

16. A method for performing hysterosalpingography on a patient, said method comprising:

providing a catheter assembly including (1) an inner catheter having a balloon near its distal end and (2) a sleeve catheter disposed coaxially over the inner catheter;

introducing the catheter assembly through the patient's vagina so that the balloon is positioned past the cervix and in the uterus while a distal end of the sleeve catheter remains outside of and proximal to the cervix;

inflating the balloon to seal against the cervix;

introducing contrast media through the inner catheter into the uterus;

imaging the uterus;

optionally advancing a distal end of the sleeve catheter over the inner catheter through the cervix and optionally withdrawing the inner catheter from the sleeve catheter to leave an access lumen in the sleeve catheter through the cervix into the uterus; and infusing of aspirating a fluid or material through the sleeve catheter into the uterus after the sleeve catheter has been advanced into the uterus and the inner catheter removed from the lumen of the sleeve catheter.

17. A method as in claim 16, further comprising:

introducing a uterine catheter through the lumen of the sleeve catheter and into the uterus after the sleeve catheter has been advanced into the uterus and the inner catheter removal from the sleeve catheter; and guiding a distal end of the uterine catheter to the Os at the entrance to a fallopian tube.

18. A method as in claim 17, further comprising:

passing a fallopian catheter through a lumen of the uterine catheter and into the fallopian tube.

19. A method as in claim 18, further comprising:

passing a falloposcope through a lumen of the fallopian catheter; and imaging the fallopian tube using the falloposcope.

20. A method as in claim 18, further comprising introducing contrast media through the fallopian catheter into the fallopian tube; and imaging the fallopian tube.

21. A method as in claim 16, wherein the catheter system further comprises a stiffening rod that is removably received in a lumen of the inner catheter, wherein the stiffening rod is in place when the catheter system is introduced through the vagina and cervix and is removed prior to introducing contact media into the uterus.

22. A method as in claim 21, wherein the stiffening rod is malleable and further comprising shaping a portion of the stiffening rod so that the inner catheter assumes a shape selected to match the patient's anatomy.

23. A method for performing hysterosalpingography on a patient, said method comprising:

providing a catheter assembly including (1) an inner catheter having a balloon near its distal end and (2) a sleeve catheter disposed coaxially over the inner catheter;

introducing the catheter assembly through the patient's vagina so that the balloon is positioned past the cervix and in the uterus while a distal end of the sleeve catheter remains outside of and proximal to the cervix;

inflating the balloon to seal against the cervix;

introducing contrast media through the inner catheter into the uterus;

imaging the uterus;

optionally advancing a distal end of the sleeve catheter over the inner catheter through the cervix and withdrawing the inner catheter from the sleeve catheter to leave an access lumen in the sleeve catheter through the cervix into the uterus; and a stiffening rod that is removably received in a lumen of the inner catheter, wherein the stiffening rod is in place when the catheter system is introduced through the vagina and cervix and thereafter removed.

24. A method as in claim 23, further comprising:

introducing a uterine catheter through the lumen of the sleeve catheter and into the uterus after the sleeve catheter has been advanced into the uterus and the inner catheter removal from the sleeve catheter; and guiding a distal end of the uterine catheter to the os at the entrance to a fallopian tube.

25. A method as in claim 24, further comprising:

passing a fallopian catheter through a lumen of the uterine catheter and into the fallopian tube.

26. A method as in claim 25, further comprising:

passing a falloposcope through a lumen of the fallopian catheter; and imaging the fallopian tube using the falloposcope.

27. A method as in claim 25, further comprising introducing contrast media through the fallopian catheter into the fallopian tube; and imaging the fallopian tube.

28. A method as in claim 23, further comprising infusing of aspirating a fluid or material through the sleeve catheter into the uterus after the sleeve catheter has been advanced into the uterus and the inner catheter removed from the lumen of the sleeve catheter.

29. A method as in claim 23, wherein the stiffening rod is malleable and further comprising shaping a portion of the stiffening rod so that the inner catheter assumes a shape selected to match the patient's anatomy.

* * * * *